United States Patent [19]

Ouaknine

[11] 4,163,319
[45] Aug. 7, 1979

[54] DENTAL OCCLUDER

[76] Inventor: Gilbert Ouaknine, 6, rue Mazzini, 11100 Narbonne, France

[21] Appl. No.: 805,472

[22] Filed: Jun. 10, 1977

[30] Foreign Application Priority Data

Jun. 11, 1976 [FR] France .................. 76 18350

[51] Int. Cl.² ........................................ A61C 11/00
[52] U.S. Cl. ..................................................... 32/32
[58] Field of Search ............................................. 32/32

[56] References Cited

U.S. PATENT DOCUMENTS

| 243,517 | 6/1881 | Cruttenden | 32/32 |
| 2,535,146 | 12/1950 | Lyons | 32/32 |
| 2,644,233 | 7/1953 | Shmukler et al. | 32/32 |
| 3,221,408 | 12/1965 | Scullin | 32/32 |
| 3,653,126 | 4/1972 | Hansen | 32/32 |
| 3,844,040 | 10/1974 | Willis | 32/32 |

FOREIGN PATENT DOCUMENTS

| 544125 | 9/1927 | Fed. Rep. of Germany | 32/32 |
| 1274790 | 8/1968 | Fed. Rep. of Germany | 32/32 |
| 172225 | 12/1921 | United Kingdom | 32/32 |

Primary Examiner—Russell R. Kinsey
Assistant Examiner—John J. Wilson
Attorney, Agent, or Firm—Shlesinger, Arkwright, Garvey and Dinsmore

[57] ABSTRACT

A dental occluder comprising top and bottom arms having base elements and matrix supports secured to each of the arms, the matrix supports each being angularly adjustable relative to the base elements and the respective arms, and the matrix supports being readily detachable from the base elements without alteration of the angular relationships of the base elements, the arms, and the matrix supports.

10 Claims, 5 Drawing Figures

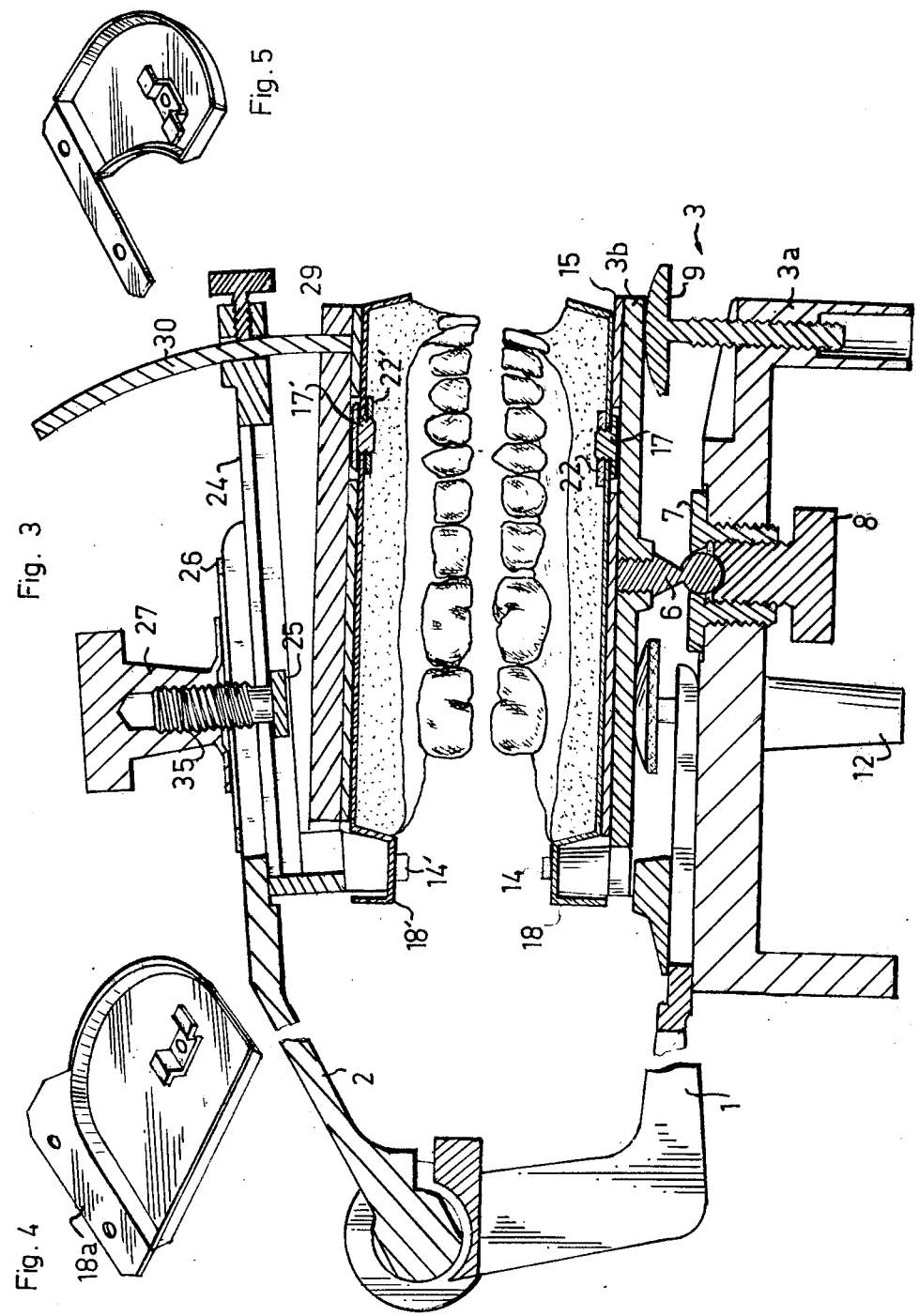

DENTAL OCCLUDER

The invention concerns a dental occluder which will put the bottom and top maxillary impressions in occlusion.

It is known that a dental occluder is an apparatus intended to hold the maxillary impressions in their natural position, facing each other, to permit a prosthetist access to work on them; these impressions are carried by two arms which are articulated together in such a manner as to reproduce the physiological movements of the jaws, particularly the opening and closing movement.

The traditional type of occluder comprises two forked arms, and is used such that each impression is cast separately and is trimmed once the plaster is dry to put it in the proper form, and then they are brought together and pressed together to study the plane of occlusion and suitable position of occlusion. Then the two impressions are held in this position by means of a bundling wire, to cast a plaster base around the foundation of each impression, in which base is sunk one arm of the occluder, and finally the bundling wire is cut. The maxillary impressions mounted on each arm can thus pivot relative to each other and close against each other in the correct occlusion position.

The work method wherein the traditional occluders are used is extremely long and tedious, particularly because of the fact that it requires preparation and casting of the plaster in two successive phases.

Besides, during the drying periods of the plaster bases the occluders are immoblized, so the prosthetist must work on a large number of apparatuses at the same time in order to avoid waste of time. Moreover, the dried plaster of the impression adheres poorly with the newly cast plaster of the base and it happens frequently in the course of settings that the impressions detach from the bases, which necessitates their remounting and causes considerable time loss.

Another type of occluder exists which in itself deletes the casting phase of the base. Use of this type of occluder, not often used because of its price, consists of casting the impressions on a rubber plate with lugs; these serve to form the centering holes in the plastic and to position a ferromagnetic disk which is provided with retention clamps, which is fixed in the plaster at the foundation of the base. The arms of the occluder have magnets with lateral lugs which permit holding and positioning of the impressions with the disk and the centering holes in the base. To find the position of occlusion, each arm is separated into two arms which are connected by a swivel joint, and means for locking the swivel joint are provided to render each arm indeformable when the proper occlusion position is found.

The major fault of this apparatus is that it is of complex structure which is costly and cumbersome, which makes work on the impressions more difficult, and moreover the arms of the swivel joint are sometimes set in unusual positions which force the prosthetist to work on the impressions at impractical angles. Additionally, the lugs of the rubber plate wear out rather rapidly and, after a certain period of use, the centering holes are deformed so that the impression cannot be easily put in place on the occluder. The result is often a poor positioning of the impression and the poor position can lead to slight variation in the course of handling, so that the occlusion is no longer perfect. Moreover, in some cases, the impression is poorly centered on the rubber plate relative to its disk and its stability can be compromised when it is mounted on the occluder. It is to be noted that the disks are often detached from the base, which necessitates a new plaster casting U.S. Pat. No. 2,644,233 discloses an occluder of simpler structure than the preceding but which has certain of the same disadvantages and some additional disadvantages. The maxillary impressions are each cast around a small plate which is sunk in the impression, in this occluder, and which then serves to fix it on the corresponding arm. The casting of the impressions around these small plates is a delicate and long operation and the risk remains that they detach themselves from the impressions, which requires as before new execution of a plaster casting. Moreover, here still, the impression can be poorly centered around its small plate, which can compromise its stability and can sometimes prevent arrangement of the two impressions in a correct occlusion position.

Further, in the occluder of the U.S. patent, the position of occlusion is sought with a swivel joint device, which is difficult to block adequately, and the relative position of the impressions is liable to variation in the course of handling. It is also to be noted that the prosthetist can, if desired, detach the impression and its small plate from the occluder and put it back in place, but these operations require unscrewing or screwing of a screw.

The present invention proposes overcoming the known inconveniences of known devices by furnishing a simple structure which lends itself to rapid mounting of the impressions and then permits convenient work on them.

One essential object of the invention is to render the casting of the impressions much easier and more rapid, without necessitating casting in several phases, or mounting of extra casting accessories in the occluder, or even in the plaster of the disks, small plates or other elements.

Another object is to be able to almost instantaneously proceed with the withdrawal of the maxillary impressions and their return to the occluder always in precisely the same position.

Another object is to absolutely eliminate all risk of even slight modification of the position of the impressions when the occlusion position is found, and also all risks of accidental detachment which would lead to loss of the occlusion position.

Another object is to furnish an occluder which permits arrangement of the two maxillary impressions in their correct occlusion position in all cases, even if the castings have been effected very imprecisely.

Another object is to guarantee correct centering of the impressions without particular precaution at the time of casting.

Another object is to furnish an occluder which permits, in the same conditions, work both on the forward areas of the maxillary impressions and also on the rear areas, particularly in the case of children's mouths.

To facilitate comprehension, the terminology used assumes that the occluder is in its customary position, the impression of the top maxillary is situated over the impression of the bottom maxillary; the terms transverse or anteroposterior, referring to the corresponding areas of the plate.

The dental occluder according to the invention comprises:

two arms, bottom and top, articulated together, a bottom base element fastened to the bottom arm and provided on its top surface with magnetic means and centering structures which are hollowed out or in relief, a bottom matrix support, its surface limiting a hollow for the casting of the bottom maxillary impression and provided with means for retaining the impression in this hollow, and said matrix support includes magnetic means adapted to cooperate with those of the bottom base element and centering structures connected with those of the bottom base element, a top base element provided with magnetic means and centering structure hollowed out or in relief, on its bottom face, adjustable connection means between the top base element and the top arm, comprising a slide plate which is fastened in the anteroposterior direction on the top surface of the top base element, a block connected to this slide plate and integral with a shaft which emerges over the plate, and means for holding and locking, cooperating with said shaft and said slide plate to hold the top arm and to lock it in relation to the top base element, a top matrix support, its bottom face limiting a hollow for the casting of the top maxillary impression and provided with means to retain the impression in this hollow, said matrix support having magnetic means to cooperate with those of the top base element and centering structures connected with those of said top base element.

The arms of the occluder can be stantard arms, particularly forked arms, as are customarily used by prosthetists. They can also be arms fitted to the occluder, integral by their construction with the corresponding base elements.

The following description is in reference to the attached drawings which show one embodiment which is nonlimiting and which will facilitate understanding of the invention.

FIG. 3 is an axial vertical cross section in larger scale of the entire apparatus.

FIGS. 4 and 5 are perspective views of other types of matrix supports which can be equipped with this occluder.

Figure 1:
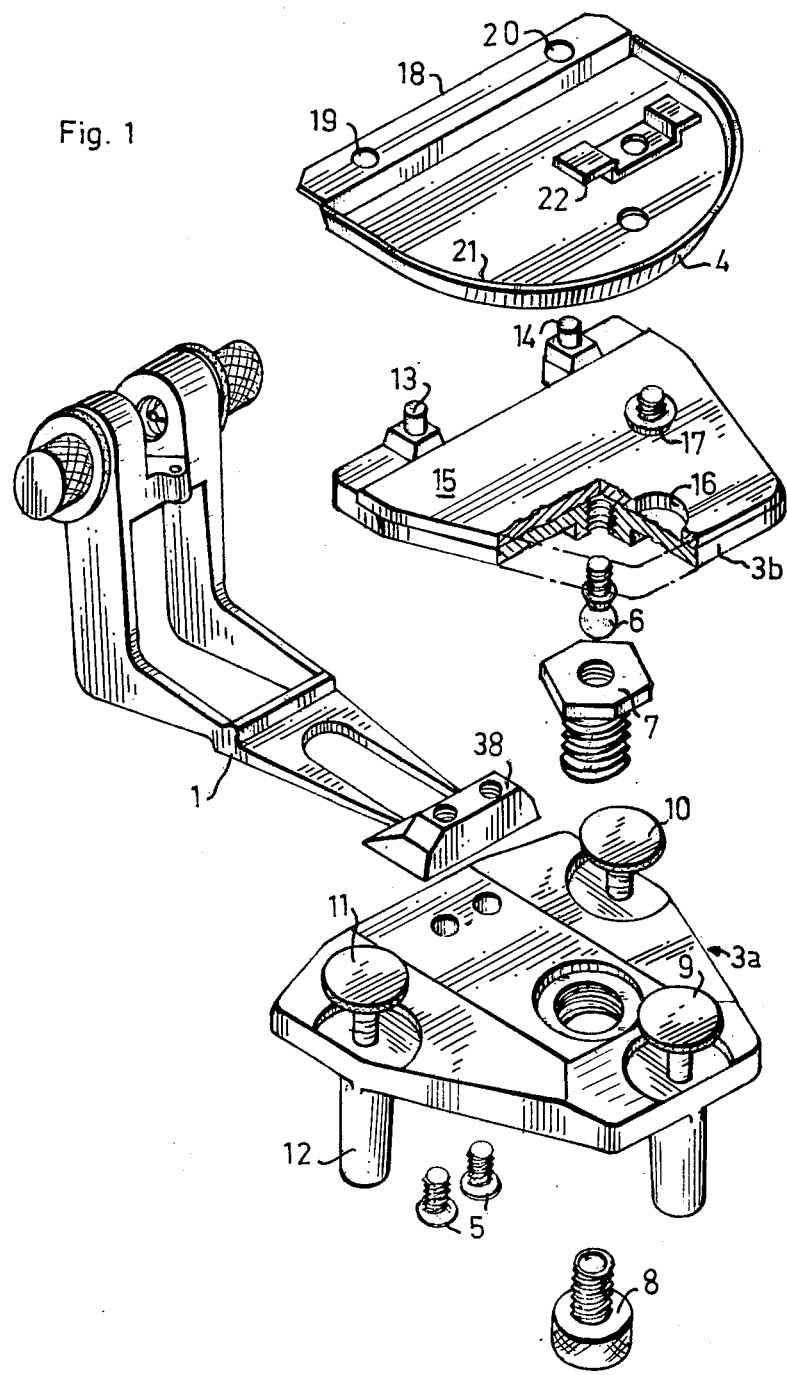
FIG. 1 is an exploded perspective view of a bottom half of the occluder according to the invention.
Figure 2:
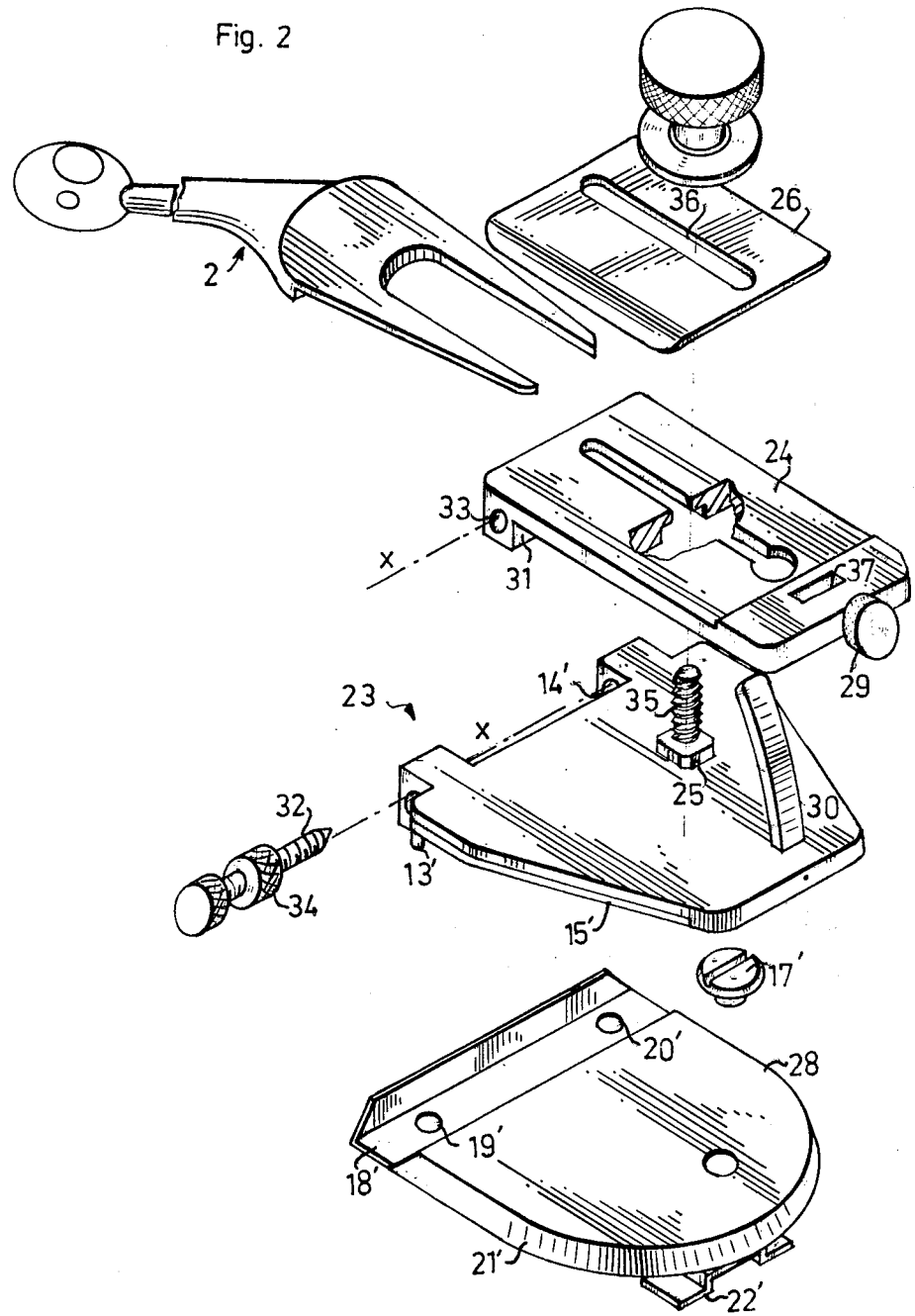
FIG. 2 is an exploded perspective view of the top half of this occluder.

The occluder shown in the example in FIGS. 1, 2 and 3 is composed of a bottom half (FIG. 1) and a top half (FIG. 2) which are articulated relative to each other by means of a bottom arm 1 and a top arm 2 of the standard fork type which is commercially available.

The bottom half of the occluder (FIG. 1) comprises a bottom base element 3 which is to be fastened to arm 1 and a bottom matrix support 4 carried by this case.

Bottom base element 3 is composed of two superposed plates 3a and 3b; bottom plate 3a is connected to bottom arm 1 by clamping and locking by means of a fixation plate 38 and by at least one screw 5, screwed in said plate and in plate 3a.

The other plate 3b is movable in relation to plate 3a and connected to it by articulation and locking means which permit it to be fixed in an adjustable angular position in relation to plate 3a. In the example, these means are constituted on the one hand of a swivel joint element 6 attached under plate 3b which can pivot in an element with spherical cup 7 which is fastened to plate 3a, and on the other hand by a locking screw 8 of this swivel joint element, and finally by three screws 9, 10 and 11, each provided with a head for handling; these screws 9, 10 and 11 are found at the top of a triangle surrounding swivel element 6 and equipped to lock plate 3b in relation to plate 3a in any angular position chosen around the pivot point of the swivel joint element, by being pressed against the bottom face of plate 3b. To give them a sufficient clearance, these screws are arranged in the formation of feet 12 on the bottom plate.

Plate 3b of the bottom base element has two centering lugs 13 and 14 at its rear, which project over its top surface; this surface is covered with a magnetic plate 15 which is adhered thereon.

This plate has an opening 16 to provide a lodging for the head of a screw 17 which serves to hold the cast impression on matrix support 4.

The matrix support is constituted of a ferromagnetic cup, for example a swaged steel cup, which has a rim 18 at the rear, provided with two centering openings 19 and 20 which are intended to cooperate with lugs 13 and 14. This generally semicircular cup is provided with raised edges 21 to limit a hollow for the casting of the maxillary impression.

The cup in FIGS. 1 and 2 shows rim 18 situated opposite the round part of the cup in order to position the cup with its circular part in front of the occluder. This model is intended for normal work on an adult maxillary impression.

Another type of cup is shown in FIG. 4; the rim 18a is situated on one side of its rounded part in order to position said cup with its circular part oriented laterally in relation to the occluder; this type of cup is adapted to work on the posterior area of the impression, particularly in the case of impressions of small dimensions of children's mouths.

The cups can also be of different shape, adapted for the nature of the work to be done on the impressions (for example extending over only one part of the plate, FIG. 5). The cups are of ferromagnetic metal and will have a rim with centering openings as well as raised edges for the direct casting of the plaster.

The head screw 17 passes through the matrix support and is screwed in a spline 22 with raised wings, at the side of the impression and intended to be sunk in it at the time of casting.

Also, the top half of the occluder (FIG. 2) is composed primarily of top arm 2 provided with its articulation swivel joint, a top base element 23 with a slide plate 24, a block 25, a plate 26, a stop bolt 27, and finally a top matrix support 28.

Top matrix support 28 is identical to bottom matrix support 4 and is simply placed in a normal reversed position (when it is connected with the occluder), so that the top surface of the one corresponds to the bottom surface of the other and vice versa. FIG. 2 shows the identical references with prime superscripts to identify the elements.

The bottom face of top base element 23 has the same elements as the top face of bottom base element 3, i.e. magnetic plate 15', centering lugs 13' and 14'.

The top face of top base element 23 is adapted to permit slide plate 24 to be fastened to it by the intervention of adjustment means for its anteroposterior inclination. These means comprise on the one hand a transverse articulation situated at one end of said slide plate to permit it to pivot in the anteroposterior direction, and on the other hand, a locking element 29 situated at the other end of said slide plate and cooperating with a concave spline 30 which is integral with the base element to assure locking of the slide plate at the proper inclination. For this, this spline passes through an opening 37 in the slide plate wherein terminates the end of locking element 29.

In the example, slide plate 24 consists of a plate including a rear turnback edge 31 and an oblong opening of reversed T section, to lodge the block 25. The transverse articulation is realized by two pointed screws 32, screwed on either side at the rear of base 23 and each having a conical end pressed in a seat 33 which is in the side of edge 31 of the slide plate; a lock nut 34 is associated with each screw 32 to block it without play in the proper articulation position.

Block 25 is engaged in slide plate 24 integral with a threaded shaft 35 which emerges through the slide plate, passes in the fork of arm 2, passes through plate 26 through a button-hole 36 and comes to cooperate with locking nut 27, which is a nut provided with washer at its base. Plate 26 includes folded back edges to overlap top arm 2 and to guide its anteroposterior displacement in the course of trying to find the occlusion position.

The advantages and results which can be obtained by this occluder are shown in the description of its use.

The prosthetist casts the impression directly in the matrix support, and spline 22 is fixed in it by screw 17. The type of matrix support is chosen according to the work to be done. For the work on a complete adult impression, or for work on anterior areas on children's impressions, a cup of the type shown in FIGS. 1, 2 and 3 should be chosen.

On the other hand, for work on the posterior areas on children's impressions, a cup of the type shown in FIG. 4 should be chosen because this cup, angularly set off at 90° relative to the preceding, authorizes easy access to the posterior area of the impression.

For work on a partial impression, a cup of the type shown in FIG. 5 should be chosen.

It is to be noted that the casting is effected without particular precautions; spline 22 does not have to be in position precisely since it serves only as a retainer. The impression which is thus cast in its matrix support forms a compact entity easy to handle or to store between work periods. It is to be noted that each impression cast in the matrix support is automatically centered in relation with the matrix support, and the stability of the entire unit is assured.

The matrix support and the impression are arranged semi-instantaneously on the corresponding base element, simply by applying the matrix support on it and introducing the centering lugs into the corresponding openings. The matrix support is then firmly fixed in perfectly defined position on the base. Its removal by the prosthetist is easy by a simple force greater than the magnetic forces and its return to position, almost instantaneous, will find the matrix support in identical position.

The occlusion position is found by displacing the top base in the anteroposterior direction in relation to the arm and by giving it a suitable inclination with the needle screw articulation 32. Once the occlusion position is found, tight locking of nut 27 and element 29 guarantee a perfect nondeformability of the assembly without any possibility of even slight modification (contrary to that which occurs in the case of locking of a swivel joint which still has play).

It is to be noted that in case of appearance of play in the articulation, it can be eliminated by close tightening of needle screws 32 and lock not 34.

In case of nonparallelism being caused by imprecise casting of an impression, it is possible to position plate 3b to correct this fault, by unscrewing screw 8, forcing plate 3b to pivot so that the impressions are again in parallel planes, then by retightening nut 8 in order to lock plate 3b in this position, and by assuring definitive locking by means of three screws 9, 10 and 11.

Thus when the occluder is locked in any given position of occlusion, the prosthetist is sure to retain this position without risk of even slight modification.

It is to be noted that when the work is entirely completed, the impression can be removed from its matrix support by unscrewing screw 17. The matrix support is recovered and only spline 22 (extremely low cost, because of its imprecise form) remains with the impression. This impression can be remounted on the matrix support in an identical position since, because it was cast therein, its contours perfectly fit the inner form of the matrix support.

The occluder shown in the drawings uses standard arms 1 and 2. It is possible to provide arms fitted to said occluder. In this case, plate 26 of the top half is integral by its construction with the top arm and forms one single element with it. The other elements are identical, the locking being effected in the same manner by clamping by means of nut 27. Besides, it is analogous for the bottom half, wherein plate 3a is integral by its construction with the bottom arm and forms one single element with it. Fixation plate 38 is then of no use, and the other elements remain identical.

While this invention has been described as having a preferred design, it will be understood that it is capable of further modification. This application, is therefore, intended to cover any variations, uses, or adaptations of the invention following the general principles thereof and including such departures from the present disclosure has come within known or customary practice in the art to which this invention pertains, and as may be applied to the essential features hereinbefore set forth and fall within the scope of this invention or the limits of the claims.

What I claim is:

1. A dental occluder for placing a bottom maxillary impression and a top maxillary impression in occlusion comprising:

top and bottom arms articulated relative to each other, a bottom base element secured to said bottom arm and including first magnetic means and first centering means, a bottom matrix support including second magnetic means and second centering means, said first and second magnetic means cooperatively retaining said bottom matrix support on said bottom base element and said first and second centering means cooperatively positioning said bottom matrix support on said bottom base element.

a top base element including adjustable connection means for attaching said top base element to said top arm and further including third magnetic means and third centering means, a top matrix support including fourth magnetic means and fourth centering means, said third and fourth magnetic means cooperatively retaining said top matrix support on said top base element and said third and fourth centering means cooperatively positioning said top matrix support on said top base element, said adjustment connection means comprising a slide plate pivotally connected to an end of said top base element, for angular adjustment therebetween, said slide plate having an elongate slot therein and locking means passing through said slot for securing said slide plate to said top arm, said slide plate further including at an end opposite said pivotal connection an opening through which passes a spline extending from said top base element, and means for releasably locking the position of said spline in said opening, whereby the angle between said top base element and said slide plate, and thus said top arm, may be adjusted.

2. A dental occluder as in claim 1 and wherein each of said matrix supports comprises a cup having raised edges of generally semicircular form and a rim and wherein said second and fourth centering means comprise openings in said rims, and said first and third centering means comprise projecting lugs engageable with said openings.

3. Occluder as in claim 2, wherein the rim of each cup is situated opposite the round part of the semicircle in order to position the cup with its arcuate part toward the front of the occluder.

4. Occluder as in claim 2, wherein the rim of each cup is situated on one side of the round part of the semicircle in order to position said cup with its arcuate part to the side relative to the occluder.

5. Occluder as in claim 1, wherein said first and third magnetic means comprise a magnetic plate fixed on each base element and the corresponding matrix support is of ferromagnetic metal.

6. Occluder as in claim 1, and including retention means for holding an impression on the corresponding matrix support comprise a head screw, passing through said matrix support and screwed into a raised wing spline, situated at the side of the impression and embedded in the impression during its casting.

7. Occluder as in claim 1, wherein said locking means comprises a clamp plate applied on the top arm and a bolt and locking nut screwed on top of the plate on the threaded shaft of the bolt, for clamping the top arm between the slide plate and said clamp plate.

8. Occluder ad in claim 1, wherein said bottom base element comprises a bottom plate connected to the bottom arm and a top plate having said first magnetic means and said first centering means, said top plate being movable in relation to the bottom plate and connected to it by articulation and locking means so that said top plate can be fixed in an adjustable angular position relative to said top plate.

9. Occluder as in claim 8, wherein the articulation and locking means of the two plates comprise a swivel joint element connecting the two plates and means for locking said swivel joint element, and three screws situated in a triangle surrounding said swivel joint element and adapted to permit locking of one plate in relation to the other in any angular position around the pivot point of the swivel joint element.

10. Occluder as in claim 8 wherein said bottom plate of the bottom base element is fastened to said bottom arm by means of a fixation plate and at least one screw screwed in the fixation plate and in the bottom plate in order to clamp and lock the arm between said plates.

* * * * *